United States Patent [19]

Frey et al.

[11] 4,381,922
[45] May 3, 1983

[54] COMBUSTION DETECTING DEVICE USING METALLO-PHTHALOCYNINE SEMICONDUCTOR AND PROCESS OF PREPARING SAME

[76] Inventors: Yvan A. R. Frey, Rue de la Coupe 22, 7000 Mons; Andre P. Z. De Haan, Avenue Lemiex 35, 7020 Mons-Hyon, both of Belgium

[21] Appl. No.: 258,516

[22] Filed: Apr. 28, 1981

Related U.S. Application Data

[63] Continuation-in-part of Ser. No. 9,158, Feb. 2, 1979, abandoned, which is a continuation-in-part of Ser. No. 884,402, Mar. 8, 1978, abandoned.

[30] Foreign Application Priority Data

Mar. 11, 1977 [LU] Luxembourg .................... 76937

[51] Int. Cl.$^3$ ........................................... G01M 27/62
[52] U.S. Cl. .......................................... 422/98; 73/23; 340/628; 427/82; 148/175
[58] Field of Search ............... 23/232 E; 422/91, 92, 422/98; 338/13, 22.5 D, 34; 324/71 SN; 73/23, 27 R; 340/579; 427/82; 148/175; 156/612

[56] References Cited

U.S. PATENT DOCUMENTS

| | | | |
|---|---|---|---|
| 3,428,892 | 2/1969 | Meinhard | 338/34 X |
| 3,497,323 | 2/1970 | Neubert | 422/96 |
| 3,616,677 | 11/1971 | Oppegaard | 422/96 X |
| 3,645,999 | 2/1972 | Byrd | 422/83 X |
| 3,999,122 | 12/1976 | Winstel et al. | 23/232 E X |
| 4,093,562 | 6/1978 | Kishimoto | 313/103 CM X |

Primary Examiner—Norman Yudkoff
Attorney, Agent, or Firm—Robert E. Burns; Emmanuel J. Lobato; Bruce L. Adams

[57] ABSTRACT

A device for detecting combustion products and effects resulting from combustion is made by preparing a composition of metallo-phthalocyanine in amorphous or crystaline form selected from the group of $Fe_{II}Pc$, $Fe_{III}Pc$, $Ni_{II}Pc$, $Cu_{II}Pc$, $CuPc-CCl_4$ where Pc represents phthalocyanine, mixing the metallo-phthalocyanine in powder form with a carbon-containing solvent and allowing it to remain in the solvent for a period of time to modify its initial phthalocyanine molecule, stirring the mixture to provide a suspension of the modified composition in the solvent, applying a thin uniform coating of such suspension in a selected pattern on an insulating substrate and drying the coating to form a resistance element having a resistance between $10^6$ ohms and $10^{10}$ ohms. Electrical contacts are provided for connecting such resistance element into an electrical circuit for measuring its electrical resistance and thereby detecting change of electrical resistance produced by exposure to combustion products and effects resulting from combustion.

14 Claims, 10 Drawing Figures

COMBUSTION DETECTING DEVICE USING METALLO-PHTHALOCYNINE SEMICONDUCTOR AND PROCESS OF PREPARING SAME

REFERENCE TO PRIOR APPLICATIONS

This application is a continuation-in-part of our application Ser. No. 9,158 filed Feb. 2, 1979 as a continuation-in-part of application Ser. No. 884,402 filed Mar. 8, 1978 (both now abandoned).

FIELD OF INVENTION

The present invention relates to a process for preparing and bringing into use organic semi-conductors which after modification of the properties thereof under various actions are able to be directly used in measuring devices for measuring the electrical resistance designed for the qualitative and quantitative detection of combustion gases or changes in temperature, or also modifications in the composition of the atmosphere due to the presence of strange gases.

BACKGROUND OF THE INVENTION

It is generally accepted that a good semi-conductor should have a certain number of essential characteristics if it is to function well, the most obvious characteristics being:

(a) a large variation in resistance under the action of the agents considered separately or otherwise;
(b) the lowest possible detection threshold;
(c) a resistance that is in a range compatible with a reliable electronic circuitry and if possible with one that is not expensive, for the higher the resistance, for example greater than $10^{10}\Omega$, the more costly will be the necessary electronic circuitry and the more the stray current phenomena (induction) will interfere with the measurements; on the other hand, if this resistance is too low, for example lower than $10^6\Omega$, the response to the agents will become extremely low and the detection threshold will be too high.

Various detection systems are already known, and they may be arranged in three broad categories based on the following principles:

the detection of fumes and smoke from combustion results from a variation in the current produced in a photocell which reacts during the passage of the smoke through its light path. Various more or less sophisticated systems have been produced on this basic principle, in which for example at least two photocells connected in a bridge circuit, chemical products added to make the smoke less transparent, or one or more smoke passage chambers have been used . . . ;

the use of the Tyndall effect of lateral diffusion of the detection light to show changes in radiation;

the smoke, fumes and gases from a combustion are detected by means of ionized preparation or radioactive substances.

BRIEF DESCRIPTION OF DRAWINGS

In the following description of the invention, reference will be made to the accompanying drawings in which.

DESCRIPTION OF THE INVENTION

Figure 1:
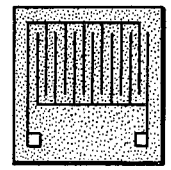
FIG. 1 is a schematic illustration of a device in accordance with the invention.

The present invention provides a process for preparing and bringing into use organic semi-conductors designed for the qualitative and quantitative detection of the presence in the atmosphere of gases formed by complete or incomplete combustion comprising in particular carbon containing products such as CO, $CO_2$, R—CHO, $R_2$—CO, R—COOH, sulphur oxides, nitrogen oxides, hydrochloric acid (HCL), hydrocyanic acid (HCN), ammonia ($NH_3$), water ($H_2O$) . . . , of changes in temperature, of infra-red irradiation, or of modification in the composition of the atmosphere due to the presence of strange gases, wherein the detection is based on the variation in the electrical resistance of at least one type of organic semi-conductors chosen in the porphyrins and in particular phthalocyanines, bonded or not to a central element well chosen in all the metals such as sodium, magnesium, tin, iron, nickel, cobalt, copper, manganese, cerium, etc. . . . , and wherein a highly accurate detection is carried out based on one or more parameters.

The phthalocyanines (symbolised by Pc) and the porphyrins (symbolised by P) will be of the type:

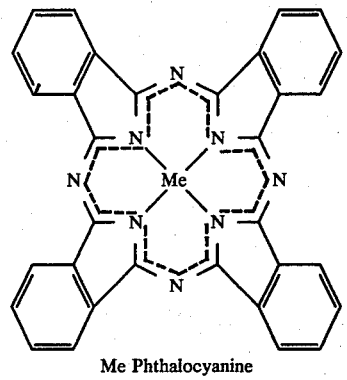

Me Phthalocyanine
PcMe

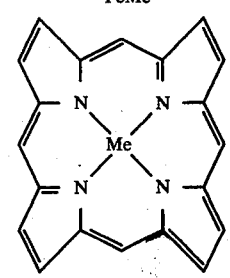

Me Porphyrin
Pme

These materials may be used either in an amorphous state or in a crystalline state in each of their crystallographic forms, though of course the variation in resistance to the action of various agents will differ widely.

The oxidaton state of the central metal elements may be any one of the possible values, and for example the following materials may be considered:

| | |
|---|---|
| Fe$_{II}$Pc | (iron II phthalocyanine) |
| Fe$_{III}$Pc | (iron III phthalocyanine) |
| Cu$_{II}$Pc | (copper II phthalocyanine) |
| CuPc | (metallic copper phthalocyanine). |

In order to meet the various criteria specified above as well as particular criteria, various physical and chemical factors may be modified during the preparation of the semi-conductors, namely:

the synthesis of the compound may (or not) be followed by a heat treatment so as to obtain the crystallographic form that best corresponds to the criteria;

mixtures of different metal phthalocyanines may be made so as to adjust the value of the resistance to the desired range, while maintaining high percentages of changing and annuling the action of some gaseous agents by the choice and the proportions of phthalocyanines having opposed or complementary effects on the resistance so as to obtain a good selectivity opposite other agents. Thus, for example, a preparation may be made insensible to the presence of ammonia by compressing a mixture of nickel II phthalocyanine and iron II phthalocyanine (ratio 1:3). Indeed the resistance of nickel phthalocyanine increases in the presence of ammonia while that of iron phthalocyanine decreases. By a correct proportion, the effect is annuled in the presence of ammonia while the sensibility in the presence of nitrogen oxides for example is entirely preserved;

the phthalocyanine molecule may be modified either by adding co-ordinating groups such as chloranil, pyridine, tetracyanoquinodimethane, paraphenylene-diamine, carbon tetrachloride, etc. . . . , or by substituting one or more carbon atoms in each peripheral benzene ring by nitrogen, for example:

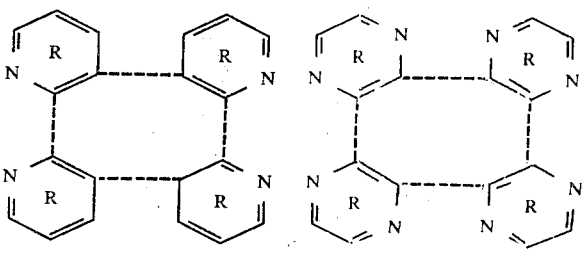

in order to establish a desired resistance range. In some cases, the co-ordinating groups may be added directly by the bringing into use. Thus, for example, carbon tetrachloride (CCl$_4$), ether ((C$_2$H$_5$)$_2$O), acetone ((CH$_3$)$_2$CO), etc. . . . are not only compounds which modify the initial molecule while being added to it and modifying the properties thereof, but they are also base solvents in the case of application by painting.

Figure 2:
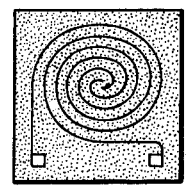
FIG. 2 is a schematic illustration of another form of device.

Depending on the application of the compounds, the semi-conductors made may differ widely. They may be formulated as powders consisting of one or the other phthalocyanine taken separately or as a mixture before or after the addition of the coordinating groups and deposited on an insulating carrier provided with electrical contacts enabling the resistance of the powder to be measured. This carrier may for example consist of a printed circuit having small dimension, of the order of 1 to 3 cm$^2$, the electrical contacts of which are in the form of two overlapping combs as illustrated in FIG. 1 or two concentric spirals as illustrated in FIG. 2. A few dozen milligrams of the product are spread over this circuit and the whole is compressed under a pressure of 2 to 10 tons/cm$^2$. The higher the pressure, the greater will be the reduction of the total resistance. Thus in the case of copper II phthalocyanine crystallised in the $\beta$-form, the resistance will fall from $10^{10.2}\Omega$ to $10^{8.5}\Omega$ according as the compression will have taken place under 3 tons/cm$^2$ or 7 tons/cm$^2$.

The choice of the substrate has a considerable influence on the behavior of the detector obtained. Thus, as regards fire detection, the phthalocyanies chosen and effectively used are in a relatively high resistance range ($10^9\Omega$–$10^{10}\Omega$). Consequently, the resistance of the carrier must be at least higher by a factor of 10 than the resistance of the semi-conductive preparation.

The resistance of carriers made of epoxy resin (such as that used for making printed circuits) changes in a large extent depending on the atmosphere humidity (for instance from $10^{10}\Omega$ to $10^6\Omega$ for a relative moisture variation of 50 to 90%).

Carriers made of pure alumina that are provided with silver contacts have a rather similar behavior. We have found that this disadvantage can be overcome by using an alumina carrier covered with a very thin layer of glass with a low melting point (about 550° C.). On this glass layer is stenciled through masks a paste of a silver-palladium alloy that is then annealed for two hours to 450° C. The contacts prepared in this way are electrochemically plated with gold. We do not know the reason for the gold plating, but experience shows that the results obtained are much better. The resistance of the supports made in this way ranges between $5.10^{10}\Omega$ and $10^{11}\Omega$ and remains constant provided the relative humidity of the air does not reach 95%.

Another method of applying the compound to the substrate comprises carrying out evaporation in vacuo (sublimation) of the powder or powder mixtures on the printed circuit, and for example the combined effect of a temperature of 400° C. and a vacuum of $10^{-2}$ mm Hg is sufficient. This sublimation process has the result of increasing the total electrical resistance. Thus, for example, pure cobalt II phthalocyanine recrystallised in $\alpha$-form has a resistance of $1.6 \times 10^9\Omega$ instead of $4 \times 10^4\Omega$ under compression at 3 tons/cm$^2$ for 3 minutes.

The application of the compound on the carriers may be a means to carry out the chemical treatment by adding coordinating groups, for example by immersing the organic semiconductor(s) chosen into a solvent such as carbon tetrachloride (CCl$_4$), ether ((C$_2$H$_5$)$_2$O), acetone (CH$_3$—CO—CH$_3$), etc. . . . After a sufficient stay—of the order of 24 hours—in the solvent, the powder will be disposed on the substrate provided with electrical contacts by painting which is then dried by evaporating the excess solvent.

This mode of operating is very advantageous. Indeed, besides the fact that it results in a change of the initial molecule by conferring to it new properties, it allows to obtain a very high reproductibility in the preparation and uniformity of behavior over a period of time and to eliminate the influence of the covering thickness and consequently of the quantity of material used. Thus when operating by compression or evaporation in vacuo, for the same quantity of material (10 mgr) and all the other variables being fixed, dispersions between $5.10^8 \Omega$ and $9.10^9 \Omega$ are easily recorded in the case of copper II phthalocyanine.

On the other hand, in the case of painting with the same phthalocyanine in suspension in carbon tetrachloride, the values of the preparations are centered between $2.10^9 \Omega$ and $3.10^9 \Omega$, and this, whatever may be the number of the applied layers. Moreover, when immersed in a chlorinated solvent, the initial molecule is changed due to a reaction of the following type:

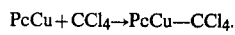

$$PcCu + CCl_4 \rightarrow PcCu-CCl_4.$$

The formation of the compound $PcCu-CCl_4$ may easily be made obvious by absorption spectrophotometry, as appearance of two new bands at 635 and 350 nm is observed. The new molecule thus formed will consequently have a different behavior. Thus, for example, when measuring the change in resistance of the circuits between an atmosphere the air of which was dehydrated with calcium chloride and an identical atmosphere with 75% relative humidity, it may be observed that the resistance of untreated copper II phthalocyanine increases by a decade (for example: $1.5 \cdot 10^8 \Omega$ to $2.2 \cdot 10^9 \Omega$) while the resistance of an identical phthalocyanine having been treated with carbon tetrachloride decreases by half a decade (for example: $6.3 \cdot 10^9 \Omega$ to $1.6 \cdot 10^9 \Omega$).

After having studied the behavior of a large number of phthalocyanines, we have found that for fire detection, best results are obtained with iron III phthalocyanine crystallised in the $\beta$-form having been treated with carbon tetrachloride $CCl_4$ for at least 24 hours. The phthalocyanine is in no way soluble in the carbon tetrachloride ($CCl_4$) but forms an addition compound the formation of which can be observed by absorption spectrophotometry. The presence of chlorine in the preparation may also be easily detected after complete evaporation of the carbon tetrachloride and drying at 200° C., by the X-ray fluorescence.

Before being used, the mixture of phthalocyanine and carbon tetrachloride (10 g/l) is continuously stirred in order to give an homogeneous suspension. Said suspension is taken by means of a drop tube and 8 of said drops are distributed onto the carrier provided with its contacts. The preparation is then dried in an oven at about 150° C. for two hours.

The detectors that have been made in this way are connected to electronic devices designed for measuring their resistance. Two different types of devices can be used.

The first one measures at the same time the resistance R and its variation in the time (dR/dt). The signal is emitted either if the R value diminishes sufficiently and reaches a predetermined threshold, or if the value of (dR/dt) becomes too high. Consequently, it is possible in this way to distinguish the natural variations due to the atmosphere, which are slow and of little amplitude, from the variations due to fire, which are markedly greater and rapid.

Figure 3:
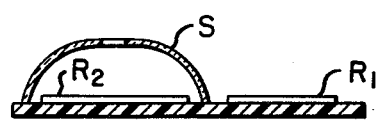
FIG. 3 is a schematic illustration of a device comprising two units of which one has an apertured transparent cover.

The device of the second type as illustrated in FIG. 3 compares the resistances of two detectors one of which one (resistance $R_1$) is in direct contact with the atmosphere, the other (resistance $R_2$) being placed behind a transparent screen S provided with a hole of about 5 mm diameter. As the resistance variations due to the atmosphere (moisture, temperature) are very slow, the resistance ratio between the two detectors $R_1/R_2$ is constant. On the contrary, when a rapid event such as a beginning fire occurs, the resistance $R_1$ changes much more rapidly than the resistance $R_2$, and the signal is emitted.

The screens between the detectors must necessarily be transparent in order that both detectors may be subjected to the same luminosity (production of a photocurrent).

The reason why the phthalocyanine treated with carbon tetrachloride is preferred is the very great sensibility to the gases formed in case of combustion and the fact that the resistance variation is always a reduction, whatever may be the kind of fire.

If, in such a case, copper phthalocyanine of the $\beta$-type also treated with tetrachloride is used, the sensibility is also very good, but the resistance variation is either an increase or a reduction according as the combustion takes place with or without flames.

Figure 4:
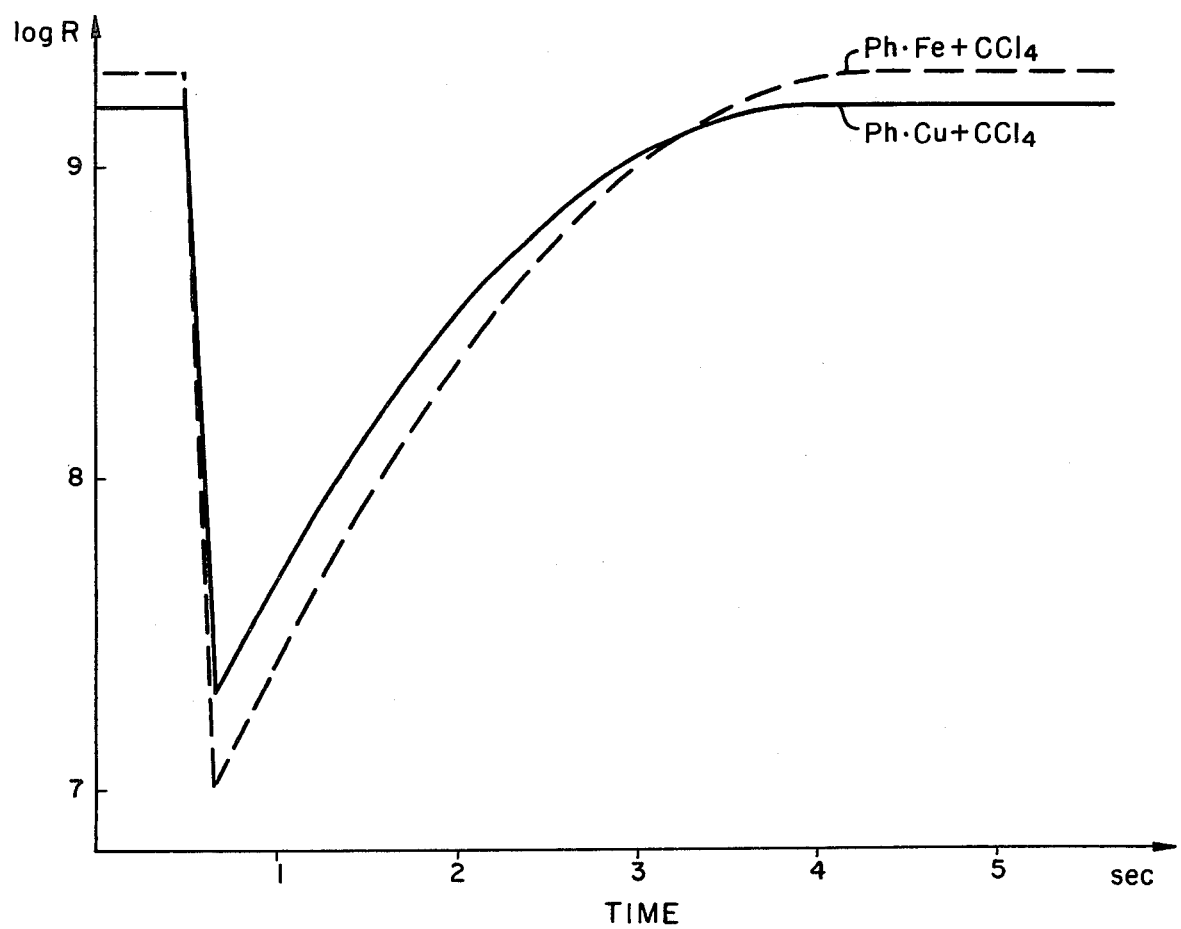
FIG. 4 shows curves illustrating change of resistance in a device exposed to combustion with flames.
Figure 5:
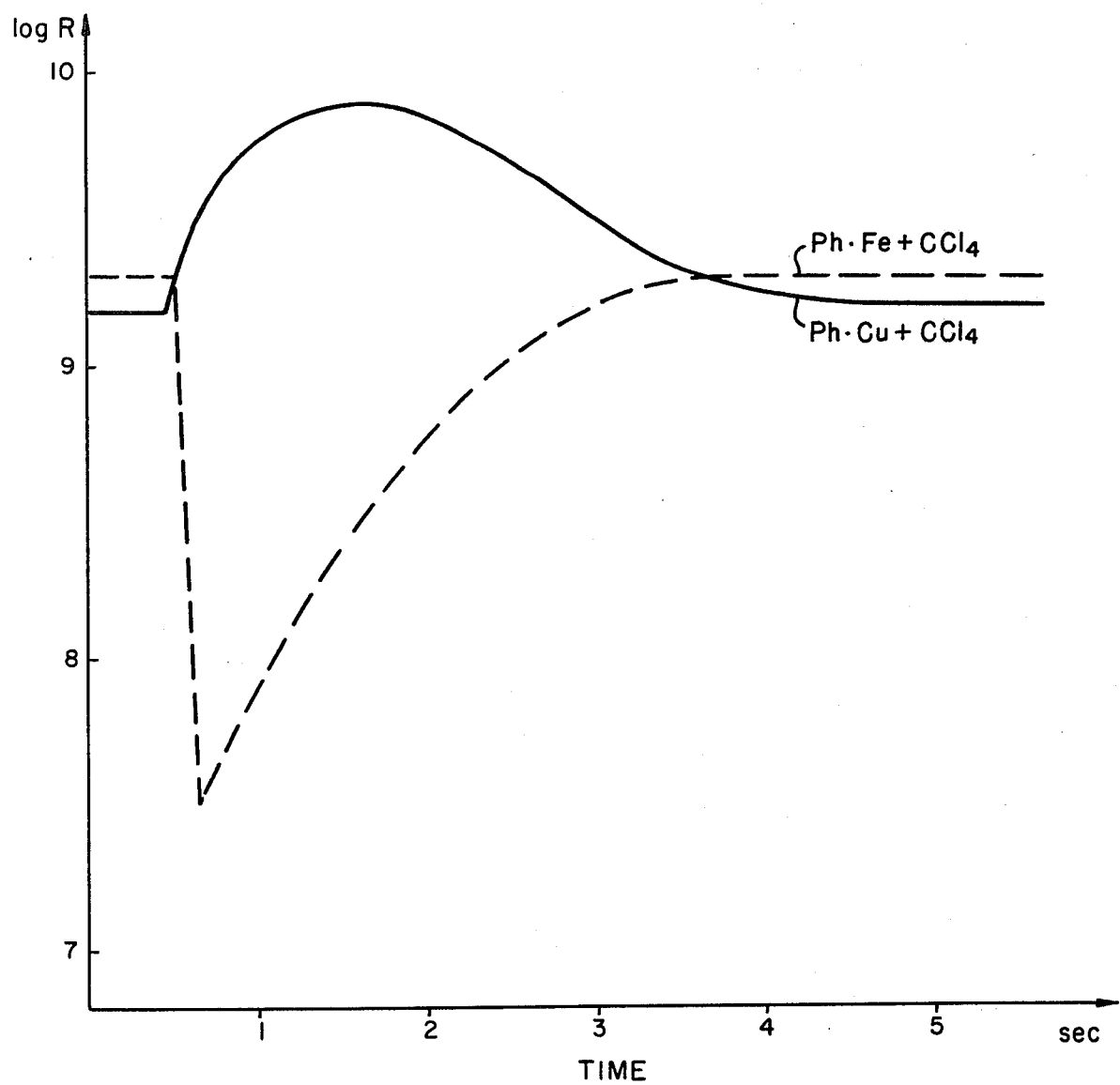
FIG. 5 shows curves illustrating change of resistance in a device exposed to combustion without flames.

FIG. 4 illustrates the change of resistance occurring in the case of both types of phthalocyanines during the combustion with flames of a sheet of journal paper of $5 \times 10$ cm in a cubic box of $0.6 \times 0.6 \times 0.6$ m. FIG. 5 illustrates the change of resistance during the combustion without flames of 1 $cm^2$ cardboard of 2 mm thickness.

Complementarily to application of the compound by painting and compression, it is possible, when the resistance of the whole preparation is too low, to bring it to the desired range by mixing the phthalocyanine, transformed or not, with an insulating material such as silica, alumina, etc. . . . , and having particle dimensions of the order of a few dozen microns. By addition of ca. 80% by weight of refractory material, the resistance is increased by a factor of 10.

Figure 6:
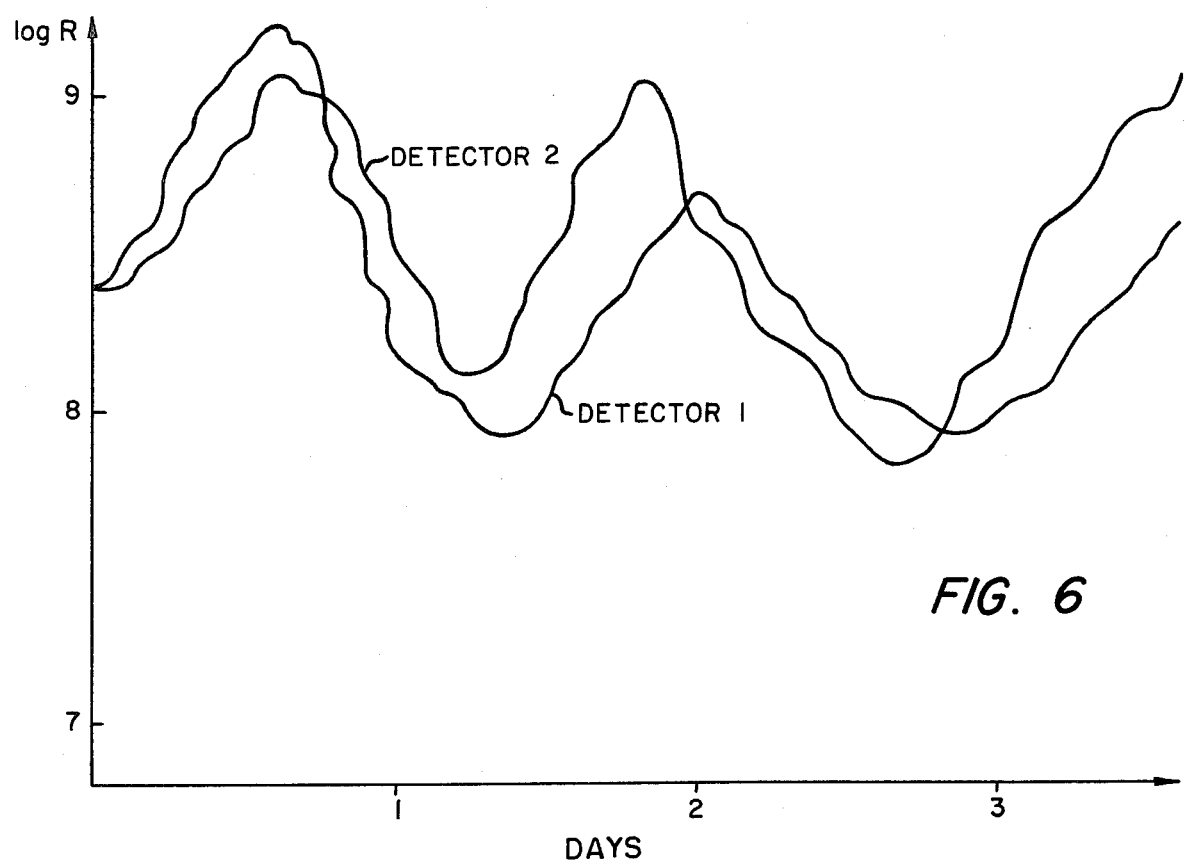
FIGS. 6 and 7 show curves illustrating the effect of humidity.

One of the problems occuring when using the detectors is due to their sensibility to the atmosphere humidity. If the evolution of the resistances of two detectors of originally the same resistance is registered over a period of time, it appears that the behaviors in the atmosphere are not quite identical and one or the other is delayed (see FIG. 6). This represents a considerable inconvenience in the case of a fire detector, for it is precisely the difference between the resistances of two detectors that is measured. As a result, the number of false signals due to humidity variations is far too great.

This drawback may be avoided in a very simple way if silicagel or a molecular sieve is introduced into the mixture of phthalocyanine and carbon tetrachloride. The silicagel or the molecular sieve to be used is previously finely ground (size: $<38\mu$) and saturated with water. 20–30 wt % of the powder so obtained in relation to the phthalocyanine, are introduced into the mixture of phthalocyanine and carbon tetrachloride.

Figure 7:
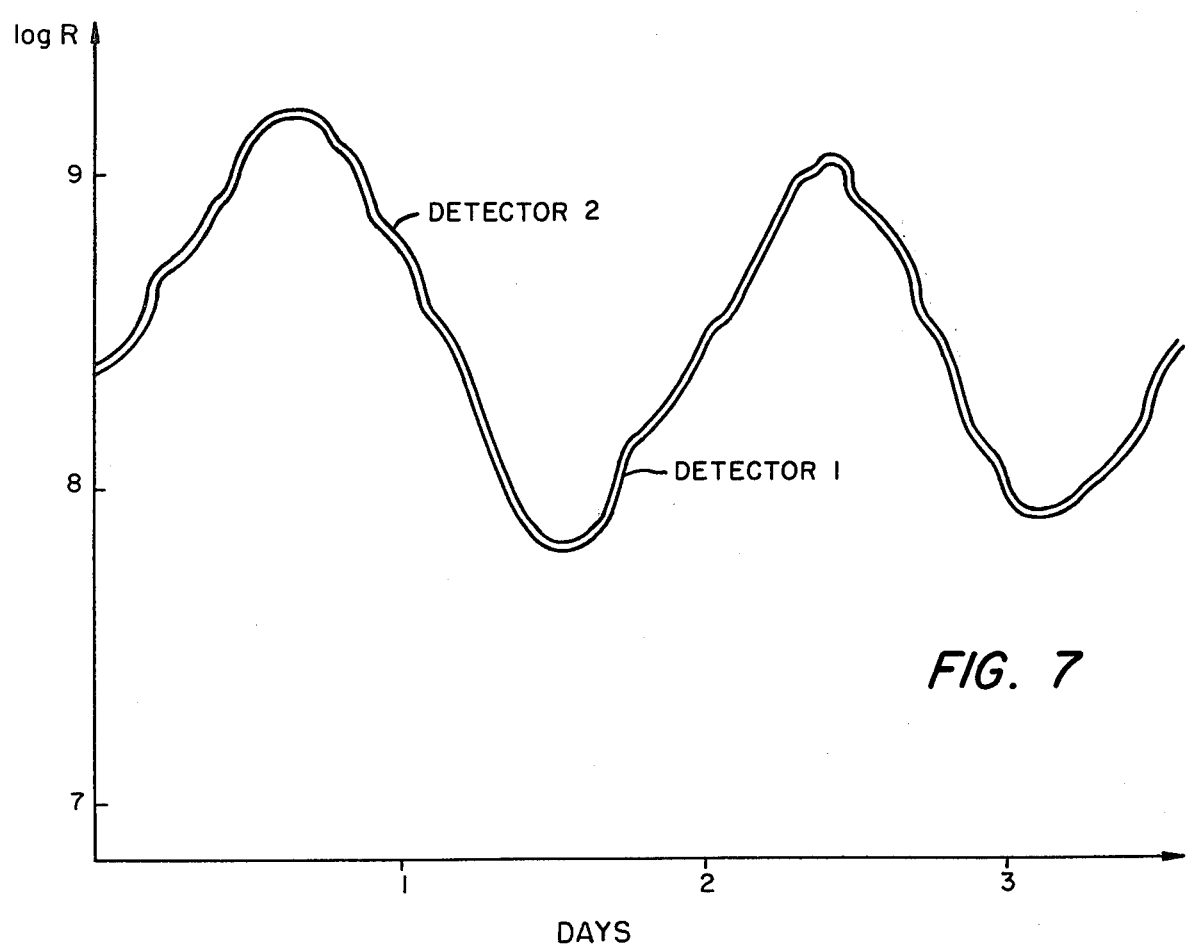

The reaction of the detectors to humidity is in this way quite stabilized, the powdered silicagel or molecular sieve acting as a buffer that regularizes the reaction of the detectors to humidity. As a result thereof, the reactions of the detectors to atmosphere humidity are quite identical, as shown in FIG. 7. The detectors that are obtained in this way remain quite sensible to the combustion gases.

Once the powders have been deposited on the carriers, they can be subjected to various activation treatments so as to improve the results or bring the resistance of the whole into a more favorable defined range, and the whole may for instance be subjected to infra-red radiation, the preparation being placed at a distance of 30 cm of an infra-red lamp of 375 W. Indeed, if during the irradiation the resistance decreases markedly then when irradiation is stopped the resistance will return to a value clearly greater than that pertaining before irradiation and for example the resistance of an iron II phthalocyanine to which 2.5% of chloranil has been added increases by a factor of 14 after having been subjected to radiation for two hours under an infra-red lamp. This irradiation causes the appearance of a photo-current due to the absorption, by certain molecules, of the radiation, and produces molecular rearrangements which alter the resistance of the whole arrangement and enable a more favorable resistance range to be obtained.

Other means of activation are also possible and comprise a heat treatment that can cause desorption of the absorbed gases and crystallographic modifications from one form to another, each form having a different specific resistance; for example at 160° C. the α-tetragonal form of phthalocyanine has a resistivity of $1.5 \times 10^4$ Ω cm, and the β-monoclinic form of phthalocyanine has a resistivity of $10^{10}$ Ω cm. Moreover, depending on the temperature and length of treatment, a greater modification from one form to another may be obtained.

By way of illustration, the following tables give the results of observations on the change in resistance of detectors corresponding to different mixtures of powders, considered as non-restrictive examples, which have been subjected to the action of different gaseous agents, infra-red radiation, temperature, and fire simulation; the tables show, below each agent to the action of which the mixture has been subjected, in the first column the percentage increase or decrease in the resistance observed, the latter being shown in the second column, with respect to the base resistance of the products in question which has been shown after each of the products; of these, the two iron II phthalocyanines correspond to two crystalline forms, the mixture of $Fe_{II}Pc$ - $CO_{II}Pc$ having been formulated in weight proportions of 2 to 1, and the mixture CuPc-chloranil containing 2.5 mole % of chloranil.

| Products | Resistance range | acetone % | R | ether % | R | petrol % | R | aldehyde % | R | methane % | R |
|---|---|---|---|---|---|---|---|---|---|---|---|
| $Fe_{II}Pc$ | $3.05 \times 10^5$ | +8 | $3.3 \times 10^5$ | +3 | $3.14 \times 10^5$ | −6.5 | $2.85 \times 10^5$ | −1.4 | $3 \times 10^5$ | −0.5 | $3.03 \times 10^5$ |
| $Ni_{II}Pc$ | $5.8 \times 10^8$ | +1 | $5.86 \times 10^8$ | +11 | $6.43 \times 10^8$ | +4 | $6.03 \times 10^8$ | −23 | $4.47 \times 10^8$ | −6 | $5.45 \times 10^8$ |
| $Fe_{II}Pc$—$Co_{II}Pc$ | $6 \times 10^5$ | +53 | $9.18 \times 10^5$ | +16 | $6.94 \times 10^5$ | −1.5 | $6.09 \times 10^5$ | −2 | $5.88 \times 10^5$ | −7.2 | $5.57 \times 10^5$ |
| $Fe_{II}Pc$ | $7.4 \times 10^8$ | +11 | $8.2 \times 10^8$ | +20 | $8.8 \times 10^8$ | +10 | $8.14 \times 10^8$ | +4 | $7.7 \times 10^8$ | −14 | $6.4 \times 10^8$ |
| CuPc—chloranil | $2.71 \times 10^3$ | +0.7 | $2.9 \times 10^3$ | — | — | +1 | $2.74 \times 10^3$ | +0.9 | $2.95 \times 10^3$ | — | — |
| $Cu_{II}Pc$ | $1.3 \times 10^8$ | −33 | $8.66 \times 10^7$ | +36 | $1.76 \times 10^8$ | +22 | $1.59 \times 10^8$ | −19 | $1.05 \times 10^8$ | −8 | $1.2 \times 10^8$ |

| Products | Resistance range | $CO_2$ % | R | HCl % | R | $NH_3$ % | R | $NO_2$ % | R | $SO_2$ % | R |
|---|---|---|---|---|---|---|---|---|---|---|---|
| $Fe_{II}Pc$ | $3.05 \times 10^5$ | +2.6 | $3.13 \times 10^5$ | −17 | $2.53 \times 10^5$ | −4.3 | $2.92 \times 10^5$ | −88.97 | $3.36 \times 10^4$ | −90 | $3.05 \times 10^5$ |
| $Ni_{II}Pc$ | $5.8 \times 10^8$ | +25 | $7.25 \times 10^8$ | −99.6 | $2 \times 10^6$ | +4150 | $2.46 \times 10^{10}$ | −99.99 | $5.8 \times 10^4$ | −99.2 | $4.64 \times 10^6$ |
| $Fe_{II}Pc$—$Co_{II}Pc$ | $6 \times 10^5$ | +3 | $6.18 \times 10^5$ | −37.3 | $3.76 \times 10^5$ | +183 | $1.69 \times 10^6$ | −96.2 | $2.28 \times 10^4$ | −89 | $6.6 \times 10^4$ |
| $Fe_{II}Pc$ | $7.4 \times 10^8$ | +17 | $8.7 \times 10^8$ | −69 | $2.3 \times 10^8$ | −69 | $2.3 \times 10^8$ | −99 | $7.4 \times 10^6$ | −99.1 | $6.66 \times 10^6$ |
| CuPc—chloranil | $2.71 \times 10^3$ | — | — | +2 | $2.76 \times 10^3$ | +155 | $6.9 \times 10^3$ | −66 | $9.21 \times 10^2$ | — | — |
| $Cu_{II}Pc$ | $1.3 \times 10^8$ | +55 | $2.2 \times 10^8$ | −46 | $7 \times 10^7$ | +344 | $5.77 \times 10^8$ | −99.9 | $1.3 \times 10^4$ | — | — |

| Products | Resistance range | $HO_2$ % | R | CO % | R | IR(46° C.) % | R | T(57° C.) % | R | Fire (32° C.) % | R |
|---|---|---|---|---|---|---|---|---|---|---|---|
| $Fe_{II}Pc$ | $3.05 \times 10^5$ | +4 | $3.2 \times 10^5$ | −35.4 | $1.97 \times 10^5$ | −92 | $2.42 \times 10^4$ | −66.7 | $1.01 \times 10^5$ | −47.8 | $1.59 \times 10^5$ |
| $Ni_{II}Pc$ | $5.8 \times 10^8$ | +6 | $6.09 \times 10^8$ | −32.8 | $7.7 \times 10^8$ | −83.8 | $9.42 \times 10^7$ | −76 | $1.4 \times 10^8$ | −54 | $2.67 \times 10^8$ |
| $Fe_{II}Pc$—$Co_{II}Pc$ | $6 \times 10^5$ | +4 | $6.24 \times 10^5$ | −6.6 | $5.6 \times 10^5$ | +80.2 | $1.18 \times 10^5$ | −78.7 | $1.31 \times 10^5$ | −25.2 | $4.48 \times 10^5$ |
| $Fe_{II}Pc$ | $7.4 \times 10^8$ | +9 | $8.06 \times 10^8$ | −50 | $3.7 \times 10^8$ | −99.1 | $6.51 \times 10^6$ | −64.4 | $2.63 \times 10^8$ | — | — |
| CuPc—chloranil | $2.71 \times 10^3$ | +1 | $2.73 \times 10^3$ | — | — | −94.5 | $1.5 \times 10^2$ | −90.2 | $2.62 \times 10^2$ | −5 | $2.57 \times 10^3$ |
| $Cu_{II}Pc$ | $1.3 \times 10^8$ | −4.2 | $7.47 \times 10^7$ | −10 | $1.17 \times 10^8$ | — | — | −46 | $6.97 \times 10^7$ | −89 | $1.46 \times 10^7$ |

By comparison with the detectors corresponding to the mixtures given by way of example, it can be seen that the resistance of the detectors constituted by copper II phthalocyanine (α-form) or cobalt II phthalocyanine (α-form) are respectively $1.5 \times 10^6$ Ω and $1.1 \times 10^3$ Ω.

The tests of changing (evolution) under the action of chemical agents were carried out in a volume of one liter in which the carrier with the chosen preparation was placed.

In the case of liquid agents, a small cotton-wool plug impregnated with the agent under examination was introduced, and in the case of gaseous agents a gas stream was passed through for about 10 seconds. The response of the detector was observed after one minute.

In the tests of changing (evolution) under the action of irradiation from an infra-red lamp, the values observed corresponded to a combination of two effects, namely heating to 46° C. and infra-red absorption.

In the tests of changing (evolution) under the action of simulated fire, a steel box having a volume of 0.21 m³ was used, in which combustion was effected with a small sheet of paper. In this case also the values observed corresponded to the combination of two effects, namely the temperature, which increased from 20° C. to 32° C., and the gaseous emanations. From the values observed during the change in resistance under the action of the heat effect alone, it may be concluded that the changes in resistance are due in roughly equal parts to each of the two effects. Furthermore, it can be established that the greatest values in the changes observed are those due to the action of the gases present in the combustion products.

It may therefore be concluded from the tables that it is possible to determine the nature, composition and activation treatments of a mixture that is perfectly adapted to the action of combustion products and temperature, given that the action of each of the latter produces a reduction in the resistance and that these actions are cumulative and such as for example in the tables the mixtures Fe$_{II}$Pc and Fe$_{II}$Pc - Cp$_{II}$Pc or modified molecules such as PcCu-CCl$_4$.

Figure 8:
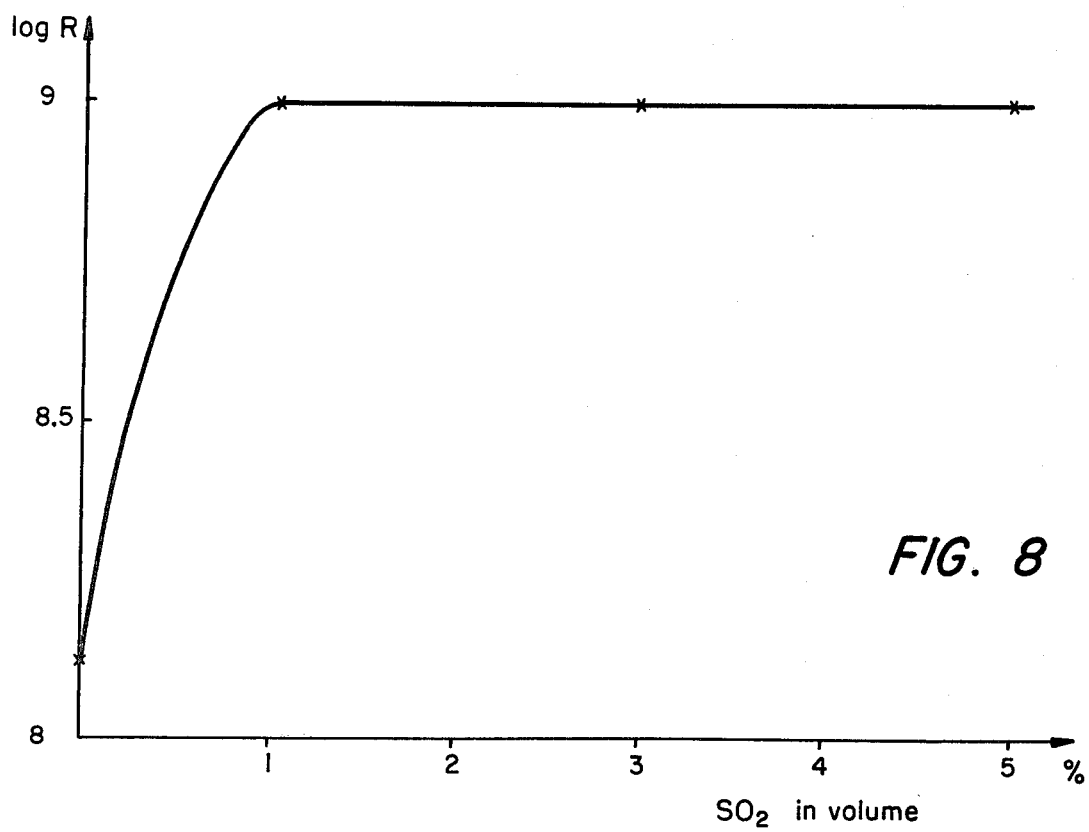
FIGS. 8 and 9 show curves illustrating the response of detectors to sulphur dioxide and nitrogen dioxide.
Figure 9:
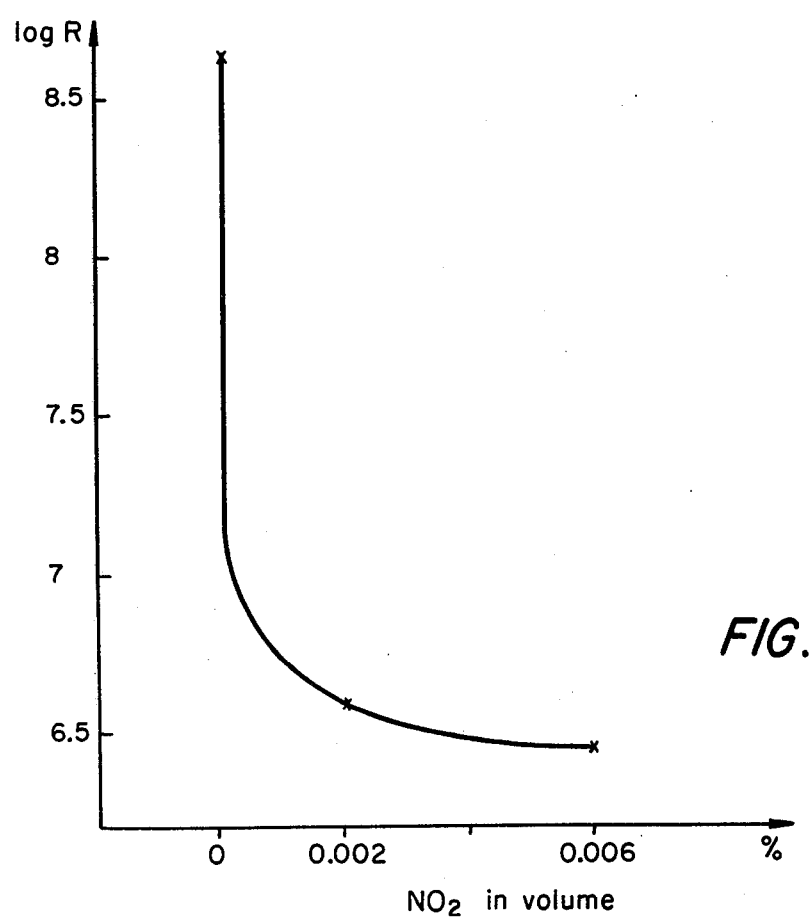

In order to show in a more precise manner the behaviour of the preparation, the graph shown in FIG. 8 represents the response to sulphur dioxide of an iron II phthalocyanine having been treated with acetone and the graph shown in FIG. 9 represents the response to nitrogen dioxide of a copper II phthalocyanine having been treated with carbon tetrachloride.

The present invention thus enables the production of preparations of organic semi-conductors which by a measurement of electrical resistance allow to very accurately detect the action of several parameters such as the composition of the surrounding gases, visible radiation and variations in temperature, so that they are effective for example in all types of combustion and thus in the case of a smouldering fire, in which the rise in temperature is only very slow but the gaseous emanations are varied and plentiful, whereas in the case of a sudden combustion the temperature rise is very rapid and the gaseous emanations are essentially carbon dioxide, water, nitrogen dioxide and sulphur dioxide.

Moreover, in order to improve still further the efficiency of this type of detection according to the invention, it is also possible to operate in a different manner, for example as follows:

two detection heads may be mounted, connected to two branches of a Wheatstone bridge, one of which, on account of the interposition of a screen (for example porous material, grille, or baffle plate) is subjected to the action of the gases and heat only after a certain time delay, and under these conditions interpretes only the percentage deviation recorded by the action of the different agents;

only a single detection head may also be used, while inserting into the electronic device a time constant that interpretes only the rate of change of resistance (dR/dt), and this only when it is negative, so that the initial resistance value may be eliminated, thus enabling a signal to be perceived only when the rate of change of resistance has exceeded a chosen threshold value. A signal due to relatively slow changes in resistance, for example natural ambient perturbations due to the action of the heating means, or variations in humidity in the atmosphere, . . . may thus be eliminated, whereas on the other hand a sudden or cumulative event due to these effects, such as fire, immediately gives rise to a signal.

The invention is not limited to its application in the field of fire detectors, and in fact by choosing a product or combination of products, activated or not, having different reactions to various agents, the process may easily used for faithfully interpreting variations of various types, for example due only to gaseous agents, or only to infra-red radiation, or also to one or the other of these combined agents.

Such detectors are also used for checking the combustion in a burner with fuel or gas and for regulating the ratio between the air and combustible quantities entering the burner.

This makes it possible to ensure a better performance and consequently to reduce the fuel used. The best results were obtained with copper phthalocyanine of the β-type treated with ether (10 g/l). The carrier is of the alumina-glass type and is provided with silver-palladium contacts.

Figure 10:
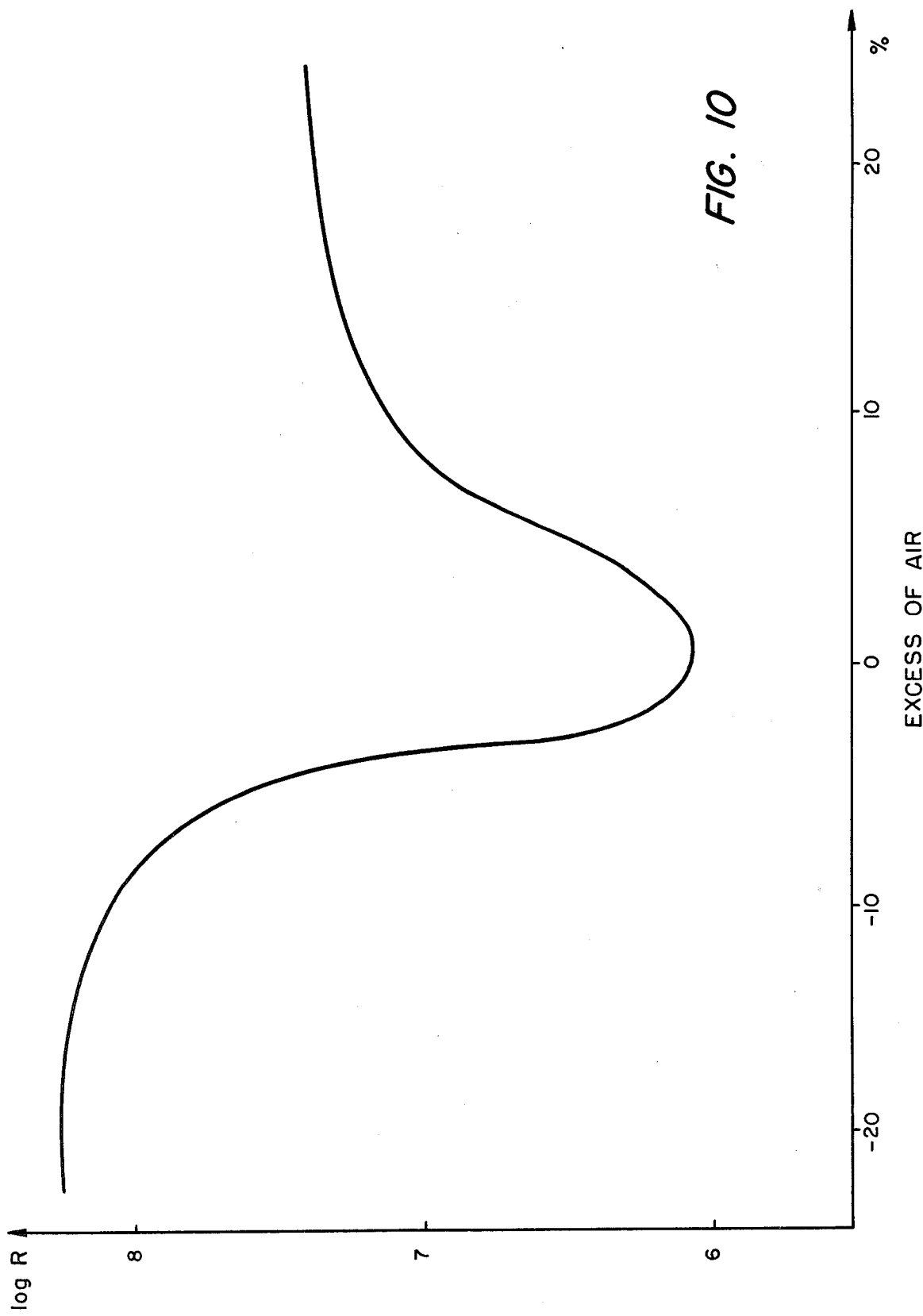
FIG. 10 shows a curve illustrating use of the device in monitoring combustion in a burner.

The bringing into use is the same as in the previous case. The detector is placed in a cell heated to the temperature of 95° C. in order to avoid the condensation of the water produced by the combustion. The smoke formed by the burner is drawn through the cell and the resistance of the detector is measured. FIG. 10 illustrates the resistance variation as a function of the coefficient of air excess (E) entering the burner.

$$E = \frac{A - A_{st}}{A_{st}} \times 100$$

wherein
A = air used
$A_{st}$ = stoechiometric air = 9.56 Nm$^3$ dry air/Nm$^3$ dry methane.

As may be seen, the curve has a minimum for a coefficient of air excess near the stoechiometry and it is now possible to adapt and regulate the admission of air to the burner.

On the other hand, the same device may be used simultaneously for indicating the presence or the absence of flames and it may consequently be substituted for the photoelectric cells with which the burners are generally provided.

We claim:

1. Process of making a device for detecting combustion products and effects resulting from combustion which comprises:

preparing a composition of metallo-phthalocyanine, in amorphous or crystalline form, selected from the group consisting of Fe$_{II}$Pc, Fe$_{III}$Pc, Cu$_{II}$Pc, CuPc-CCl$_4$ where Pc represents phthalocyanine, mixing said metallo-phthalocyanine composition in powder form with a carbon-containing liquid solvent selected from the group consisting of carbon tetrachloride, ether and acetone, allowing said metallo-phthalocyanine composition to remain in said solvent for a period of time to modify its initial phthalocyanine molecule and stirring said mixture to obtain a homogeneous suspension of the modified metallo-phthalocyanine composition powder in said solvent, applying a thin uniform coating of said suspension in a selected pattern on an insulating substrate and drying said coating to form a resistance-element having a resistance of 10$^6$ ohms to 10$^{10}$ ohms, and providing electrical contacts for connecting said resistance element in an electrical circuit for measuring the electrical resistance of said resistance element and thereby detecting change in electrical resistance produced by exposure to combustion products and effects resulting from combustion, a finely ground buffer selected from the group consisting of silicagel and a molecular sieve being saturated with water and mixed with said metallo-phthalocyanine composition before said composition is applied to said substrate.

2. A process according to claim 1, in which the phthalocyanine molecule of said composition is modified by replacing one or more carbon atoms in each peripheral benzene ring by nitrogen.

3. A process according to claim 1, in which the phthalocyanine molecule of said composition is modified by adding a coordinating group selected from the group consisting of chloranil, pyridine, tetracyanoquinodimethane, paraphenylene and diamine.

4. A process according to claim 1, 2, or 3, in which the resistance of said composition is modified by mixing two or more of said metallo-phthalocyanines.

5. A process according to claim 1, in which said phthalocyanine composition is applied to said substrate by sublimation in a vacuum at a temperature between 350° C. and 400° C. and pressure between $10^{-4}$ and $10^{-2}$ mmHg.

6. A process according to claim 1, in which the electrical resistance of said coating is modified by the application of heat.

7. A process according to claim 1, in which the electrical resistance of said coating is modified by the application of pressure in the range between 2 and 10 tons/cm$^2$.

8. A process according to claim 1, in which the electrical resistance of said coating is modified by exposure of said coating to infra-red radiation.

9. A process according to claim 1, in which said solvent is carbon tetrachloride and in which said phthalocyanine composition is allowed to remain in said solvent for a period of the order of 24 hours.

10. A device for detecting combustion products and effects resulting from combustion which comprises an insulating substrate, spaced conducting electrodes deposited on said substrate and a thin uniform coating of an amphorphous or crystalline metallo-phthalocyanine composition deposited on said substrated between said electrodes, said composition being selected from the group consisting of $Fe_{II}Pc$, $Fe_{III}Pc$, $Ni_{II}Pc$, $Cu_{II}Pc$ and $CuPc\text{-}CCl_4$ where Pc represents phthalocyanine, said coating being prepared by mixing said metallo-phthalocyanine composition in powder form with a carbon-containing liquid solvent selected from the group consisting of carbon tetrachloride, ether and acetone, allowing said metallo-phthalocyanine composition to remain in said solvent for a period of time to modify its initial phthalocyanine molecule, stirring said mixture to obtain a homogeneous suspension of the modified metallo-phthalocyanine composition powder in said solvent, applying a thin uniform coating of said suspension in a selected pattern on said insulating substrate and drying said coating to form on said substrate a resistance element having a resistance of $10^6$ ohms to $10^{11}$ ohms, said substrate having a resistance at least 10 times that of said resistance element, a finely ground buffer selected from the group consisting of silicagel and a molecular sieve being saturated with water and mixed with said metallo-phthalocyanine composition before said composition before said composition is applied to said substrate.

11. A combustion detection device according to claim 10, comprising two of said resistance elements mounted adjacent one another on a base, one of said resistance elements being exposed directly to the atmosphere and the other of said resistance elements being covered with a transparent cover having an aperture affording restricted communication with the atmosphere.

12. A combustion detecting device according to claim 10, in which said substrate comprises alumina covered with a very thin layer of glass having a melting point of about 550° C.

13. A combustion detecting device according to claim 10 or 12, in which said electrodes comprise silver-palladium alloy annealed on said substrate and electrochemically plated with gold.

14. Process of making a device for detecting combustion products and effects resulting from combustion which comprises:
preparing a composition of metallo-phthalocyanine, in amorphous or crystalline form, selected from the group consisting of $Fe_{II}Pc$, $Fe_{III}Pc$, $Ni_{II}Pc$, $Cu_{II}Pc$, $CuPc\text{-}CCl_4$ where Pc represents the monomeric phthalocyanine group,
mixing said metallo-phthalocyanine composition in powder form with a carbon-containing liquid solvent selected from the group consisting of carbon tetrachloride, ether and acetone, allowing said metallo-phthalocyanine composition to remain in said solvent for a period of time to modify its initial phthalocyanine molecule and stirring said mixture to obtain a homogeneous suspension of the modified metallo-phthalocyanine composition powder in said solvent,
applying a thin uniform coating of said suspension in a selected pattern on an insulating substrated and drying said coating to form a resistance-element having a resistance of $10^6$ ohms to $10^{10}$ ohms, and
providing electrical contacts for connecting said resistance element in an electrical circuit for measuring the electrical resistance of said resistance element and thereby detecting change in electrical resistance produced by exposure to combustion products and effects resulting from combustion,
a finely ground molecular sieve being introducted into the mixture of said metallo-phthalocyanine and carbon-containing solvent to reduce sensitivity of the device to atmospheric pressure.

* * * * *